US006468991B1

(12) United States Patent
Budowsky et al.

(10) Patent No.: US 6,468,991 B1
(45) Date of Patent: *Oct. 22, 2002

(54) METHOD OF TREATING RHINOVIRAL INFECTIONS

(75) Inventors: Edward I. Budowsky, Brookline, MA (US); Samuel K. Ackerman, Weston, MA (US)

(73) Assignee: Cyclis Pharmaceuticals, Inc., Norwood, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/784,229

(22) Filed: Jan. 16, 1997

(51) Int. Cl.$^7$ .............................................. A61K 31/675
(52) U.S. Cl. ......................................................... 514/81
(58) Field of Search ........................................... 514/81

(56) References Cited

U.S. PATENT DOCUMENTS

| | | | |
|---|---|---|---|
| 4,464,359 A | 8/1984 | Suhadolnik et al. | 424/180 |
| 4,476,301 A | 10/1984 | Imbach et al. | 536/27 |
| 4,515,781 A | 5/1985 | Torrence et al. | 514/46 |
| 4,539,313 A | 9/1985 | Suhadolnik et al. | 514/47 |
| 4,708,935 A | 11/1987 | Suhadolnik et al. | 435/91 |
| 4,859,768 A | 8/1989 | Suhadolnik et al. | 536/27 |
| 4,924,624 A | 5/1990 | Suhadolnik et al. | 47/58 |
| 4,981,957 A | 1/1991 | Lebleu et al. | 536/27 |
| 4,990,498 A | 2/1991 | Suhadolnik | 514/47 |
| 5,188,897 A | 2/1993 | Suhadolnik et al. | 428/402.2 |
| 5,405,939 A | 4/1995 | Suhadolnik et al. | 530/322 |

FOREIGN PATENT DOCUMENTS

| | | | |
|---|---|---|---|
| DE | 4211237 A1 | 10/1993 | C07H/19/20 |
| DE | 4211238 C2 | 10/1994 | |
| JP | 211596 | 1/1990 | |
| WO | WO 94/19012 | 9/1994 | |

OTHER PUBLICATIONS

Doetsch et al.; "Core (2'–5')oligoadenylate and the cordycepin analog; Inhibitors of Epstein–Barr virus–induced transformation of human lymphocytes in the absence of interferon"; *Proc. Natl. Acad. Sci. USA*, 78(11):6699–6703 (1981).

Black et al.; "2',5'–Oligoadenylate Trimer Core and the Cordycepin Analog Augment the Tumorcidal Activity of Human Natural Killer Cells"; *J. of Immunology*, 135(5):2773–2777 (1984).

Henderson et al.; "Inhibition of Epstein–Barr Virus–Associated Nuclear Antigen (EBNA) Induction by (2',5')Oligoadenylate and the Cordycepin Analog: Mechanism of Action of Inhibition of EBV–Induced Transformation"; *Short Communications*, pp. 198–201 (1982).

Torrence et al.; "Methods for the Synthesis of Analogs of (2'–5')–Oligoadenylic Acid"; *Methods in Enzymology*, 119:522–529 (1986).

Devash et al.; "Measurement of Effect of (2'–5')–Oligoadenylates and Analogs on Tobacco Mosaic Virus Replication"; *Methods in Enzymology*, 119:759–761 (1986).

Johnston et al.: "The Role of Interferon–induced proteins, double–stranded RNA and 2'–5'–oligoadenylate in the interferon–mediated inhibition of viral translation"; *Interferon*, 3(7):201–298 (1984).

Suhadolnik et al.; "Measurement of Effect of (2'–5')–Oligoadenylates and Analogs on Protein Synthesis and Growth of Cells"; *Methods in Enzymology*, 119:667–675 (1986).

Nolan–Sorden et al.; "Photochemical Crosslinking in Oligonucleotide–Protein Complexes between a Bromine–Substituted 2–5A Analog and 2–5A–Dependent RNase by Ultraviolet Lamp or Laser"; *Analytical Biochemistry*, 184:298–304 (1990).

Itkes et al.; "A route to 2',5'–oligoadenylates with increased stability towards phosphodiesterases"; *Febs Letters*, 236(2):325–328 (1988).

Liu et al.; Mechanism of interferon action, III—Significance of pppA2'p5'A2'p5'A in the Antiviral Action of Interferon, *Sci. Sin. B*, 26:809–817 (1983).

De ClercQ et al,; Antirhinovirus Activity of Purine Nucleoside Analogs, *Antimicrob, Agents Chemother*, 29:482–487 (1986).

Panicali, Effect of Cordycepin triphosphate on In Vitro RNA synthesis by Picornavirus Polymerase Complexes, *J. Virol*, 28:124–128 (1978).

Copy of International Search Report—May 27, 1998.

*Primary Examiner*—Russell Travers
(74) *Attorney, Agent, or Firm*—Ivor R. Elrifi; Barry J. Marenberg; Mintz, Levin, Cohn, Ferris, Glovsky and Popeo, P.C.

(57) ABSTRACT

The present invention provides methods for treating rhinoviral infections in a subject in need of such treatment, by the administration of 2'–5' oligoadenylates or the analogs thereof. Pharmaceutical formulations comprising 2'-5' oligoadenylates and analogs thereof are also provided.

20 Claims, No Drawings

METHOD OF TREATING RHINOVIRAL INFECTIONS

FIELD OF THE INVENTION

The present invention relates generally to a method of treating viral infections, and more specifically to a method of treating rhinoviral infections.

BACKGROUND OF THE INVENTION

Acute afebrile upper respiratory disease, often grouped clinically as "the common cold," is one of the most frequent afflictions of humans. Although the disease is typically not life-threatening, it causes much discomfort as well as the loss of over 200 million man-days of work and school each year in the United States alone. B. D. Davis et al., *Microbiology* at 1114 (Third Edition, 1980). Since 1956, when viruses from patients suffering with the common cold were first isolated, over 113 immunologically distinct, yet biologically related viruses have been isolated. Id. at 1115. The chemical and physical characteristics of these viruses led to their classification as members of the picornavirus family, and more specifically into the genus known as the Rhinoviridae, or the rhinoviruses. Rhinoviruses have been characterized as small (17–30 nm in diameter), non-enveloped, RNA-containing virions that are cubic in structure and resistant to ether treatment. It is now thought that rhinoviral infection is the cause of approximately 40 percent of all respiratory illnesses in children and adults. V. Knight, Common Viral Respiratory Illnesses, in *Harrison's Principles of Internal Medicine, Eighth Edition* at 988–990 (G. W. Thorn et al. eds., 1977).

Although several methods have been proposed as treatments for rhinoviral infection, including vaccination, air sterilization, and the administration of various pharmaceuticals, none of these methods has proved to be entirely effective. Problems that hinder the development of useful rhinovirus vaccines include the short duration of natural immunity to specific infecting types, the large number of different antigenic types of rhinovirus, and the variation of types present in a community from one year to the next. J. L. Melnick et al., *McGraw-Hill Encyclopedia of Science and Technology, Seventh Edition* 15, 454 (1992). Current methods of treatment are limited to the amelioration of symptoms, and often take the form of antihistamines and other drugs. There is therefore a desire to develop a method of treating rhinoviral infections that is effective, safe and practical.

SUMMARY OF THE INVENTION

In view of the foregoing, it is a first object of the present invention to provide a method for effectively and practically treating a rhinoviral infection.

A second object of the invention is to provide pharmaceutical formulations useful in the treatment of rhinoviral infections.

It has now been discovered that 2'–5' oligoadenylates (2',5'-A) and their analogs are surprisingly effective in the treatment of rhinoviral infections. Accordingly, a first aspect of the present invention is a method of treating a rhinoviral infection in a subject in need of such treatment. The method comprises administering to the subject a compound of Formula I:

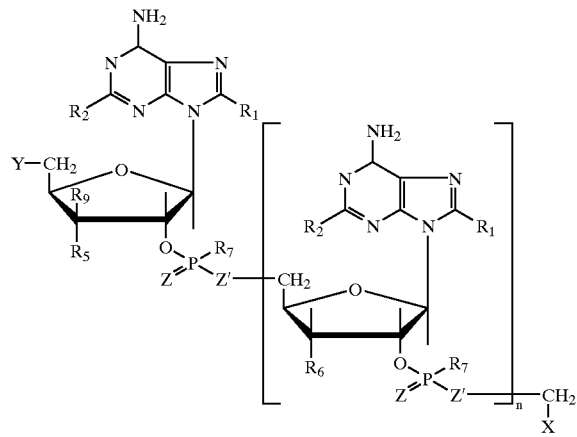

wherein n is 0, 1, 2, or 3;
each $R_1$ and $R_2$ is independently selected from the group consisting of hydrogen, halogen, and $N_3$;
each $R_5$ is independently hydrogen or —OH;
each $R_6$ is independently hydrogen or —OH;
$R_7$ is $O^-$ or —OH;
$R_9$ is hydrogen or —OH, with the proviso that when $R_9$ is —OH, $R_5$ is hydrogen;
Y is

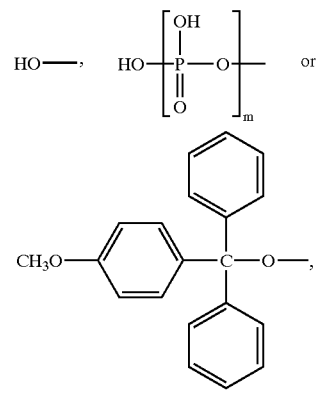

wherein m is 1, 2, or 3;
X is —CHOHCH$_2$OH, or is selected from the group consisting of

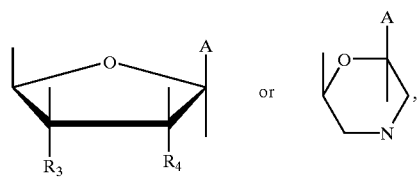

wherein $R_3$ and $R_4$ are each independently selected from the group consisting of hydrogen, —OH, and —PO$_4^{-2}$, or $R_3$ and $R_4$ together represent a cyclophosphate; and A is selected from the group consisting of

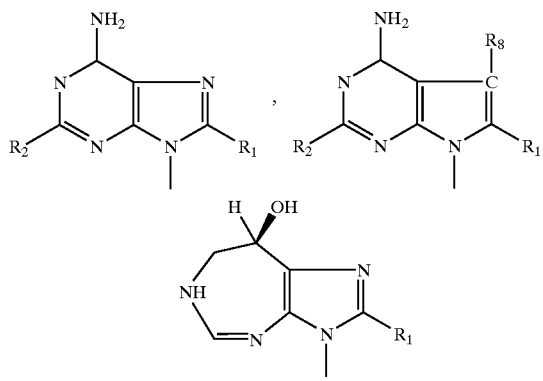

wherein each $R_1$ and $R_2$ are as provided above; and $R_8$ is selected from the group consisting of hydrogen, cyanogen, and amido;

each Z is independently O or S; and each Z' is independently O or S;

or a pharmaceutically acceptable salt thereof, (hereinafter referred to as the "active compound"), in amount effective to treat the rhinoviral infection.

In one preferred embodiment of the invention, Y is —OH. In another preferred embodiment of the invention, X is

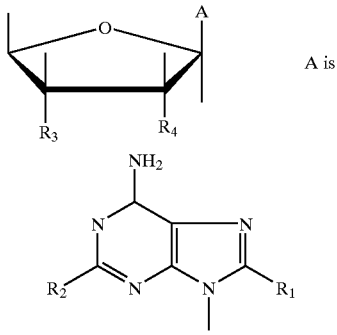

$R_1$ and $R_2$ are hydrogen;
$R_3$ is —OH and $R_4$ is —PO$_4^{-2}$, or
$R_3$ is PO$_4^{-2}$ and $R_4$ is —OH, or
$R_3$ and $R_4$ are both —OH, or
$R_3$ and $R_4$ together represent a cyclophosphate;
$R_5$ is —OH;
$R_9$ is hydrogen; and
Z and Z' are both O.

A second aspect of the present invention is a pharmaceutical formulation for combatting rhinoviral infection comprising, in combination with a pharmaceutically acceptable carrier, an active compound as described above.

A third aspect of the present invention is the use of an active compound as disclosed herein for the manufacture of a medicament useful in carrying out a therapeutic method of treatment as given above.

DETAILED DESCRIPTION OF THE INVENTION

As noted above, the methods of the present invention are useful for treating infections caused by rhinoviruses. In general, rhinovirus infections (the "condition") are characterized by nasal obstruction and discharge, sneezing, moderate sore throat and mild constitutional reaction, usually without fever. In young children, these symptoms may be further aggravated by cough, croup, and pneumonia. The methods of the present invention are useful for treating these conditions in that they inhibit the onset, growth, or spread of the condition, cause regression of the condition, cure the condition, or otherwise improve the general well-being of a subject afflicted with, or at risk of contracting the condition.

Subjects to be treated by the methods of the present invention are typically human subjects, although the methods of the present invention may be useful with any suitable subject known to those skilled in the art including mammals (e.g., horses, dogs, cats) for veterinary purposes. For example, the methods may be particularly useful in treating rhinoviral infections in performing or racing animals (e.g., greyhounds, racing horses or horses used in equestrian competitions, and circus animals).

As used herein, the term "rhinovirus" refers to viruses which are members of the picornavirus family, and more specifically to the members of the viral genus Rhinoviridiae. The rhinovirus virion is characterized as containing single stranded RNA, having a non-enveloped capsid and having cubic capsid symmetry. See Knight, supra, at 988. Rhinoviruses are sharply distinguished from other picornaviruses in that they are inactivated at low pH, maintain their infectivity at 50° C., and have higher buoyant density in CsCl. See Davis et al., supra, at 1115.

As noted above, over 113 immunologically distinct rhinoviruses (RV) have been isolated, with each individual serotype or "type" being designated by a numeral. Accordingly, rhinovirus type 1 is denoted RV-1; rhinovirus type 1, sub-type B is denoted RV-1B, etc. The present invention is useful in combatting a rhinoviral infection caused by any rhinovirus type. In a preferred embodiment, the method of the present invention is useful in combatting a rhinoviral infection caused by a rhinovirus type selected from the group consisting of rhinovirus type 1 (RV-1, including subtypes A (RV-1A) and B (RV-1B)), rhinovirus type 2 (RV-2), rhinovirus type 14 (RV-14), and rhinovirus type 39 (RV-39).

Active compounds of the present invention are, in general, 2'-5' oligoadenylates and their analogs which have anti-rhinoviral activity. In particular, active compounds of the present invention are of Formula I, as set forth above.

In one particularly preferred embodiment of the invention, the Y group of the above Formula I is —OH. In another particularly preferred embodiment of the invention, X is

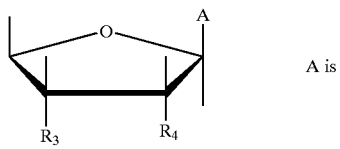

-continued

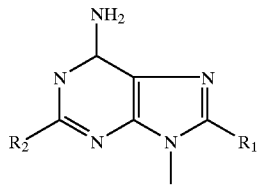

R$^1$ and R$_2$ are hydrogen;
R$_3$ is —OH and R$_4$ is PO$_4^{-2}$; or
R$_3$ is PO$_4^{-2}$ and R$_4$ is —OH; or
R$_3$ and R$_4$ are both —OH; or
R$_3$ and R$_4$ together represent a cyclophosphate;
 R$_5$ is —OH;
 R$_9$ is hydrogen; and
 Z and Z' are both O.

2'–5' oligoadenylate compounds and their analogs are known. Exemplary compounds include 2'–5' oligoadenylate, the 2',5'-oligoadenylate- 2',3' cyclophosphates disclosed in German Patent DE 42 11 237 A1 to Budowsky, et al.; the 2',5'-oligoadenylate phosphate-containing derivatives disclosed in German Patent DE 42 11 238 C2 to Budowsky et al.; the 2'- and 8-azido(2'–5')oligoadenylates disclosed in U.S. Pat. No. 4,990,498 to Suhadolnik; the 2'–5'-phosphorothioate oligoadenylates in disclosed in U.S. Pat. No. 5,188,897 to Suhadolnik et al.; the 2'–5' riboadenylate-morpholinoadenylate oligonucleotides disclosed in U.S. Pat. No. 4,515,781 to Torrence et al.; the (2'–5')-oligo(3'-deoxyadenylates) and derivatives thereof disclosed in U.S. Pat. No. 4,464,359 to Suhadolnik et al.; the 2'–5' oliogadenylate cordycepin analogs as disclosed in U.S. Pat. No. 4,859,768 to Suhadolnik et al.; the 2'–5' oligoxyloadenylates disclosed in U.S. Pat. No. 4,476,301 to Imbach et al.; and the 8-azaadenosine, sagivamycin, toyocamycin, tubericidine, and 8-bromo-adenosine analogs of 2'–5' oligoadenylates as disclosed in U.S. Pat. No. 4,981,957 to Lebleu et al. (applicants specifically intend that the disclosure of these and all other patent references cited herein be incorporated by reference herein in their entirety).

Specific compounds useful in the practice of the present invention include, but are not limited to, 2',3'-cyclophosphateadenylyl(2',5')adenylyl-(2',5')adenosine (Papirine AIII), 2',3'-cyclophosphateadenylyl(2',5')adenylyl(2',5')adenylyl-(2',5')adenosine (Papirine AIV), 2',3'-cyclophosphateadenylyl(2',5')adenosine (Papirine AII), 2'-phosphateadenylyl(2',5')adenylyl-(2',5')adenosine (Papirine BIII), 3'-phosphateadenylyl(2',5')adenylyl-(2',5')adenosine (Papirine BIII), 2'-phosphateadenylyl(2',5')adenylyl(2',5')adenylyl-(2',5')adenosine (Papirine BIV), 3'-phosphateadenylyl (2',5')adenylyl(2',5')adenylyl(2',5')-adenosine (Papirine BIV), 2'-phosphateadenylyl(2',5')adenosine (Papirine BII), 3'-phosphateadenylyl(2',5')adenosine (Papirine BII), adenylyl(2',5')adenylyl(2',5')adenosine (Papirine CIII), adenylyl(2',5')adenylyl(2',5')adenylyl-(2',5')adenosine (Papirine CIV), adenylyl(2',5')-adenosine (Papirine CII), adenylyl(2',5')3'-deoxyadenylyl (2',5')3'-deoxyadenosine and the 5' mono-, di-, and triphosphates thereof, 3'-deoxyadenylyl(2',5')31-deoxyadenosine and the 5' mono-, di-, and triphosphates thereof, adenylyl(2',5')adenylyl(2',5')tubercidin and the 5' mono-, di-, and triphosphates thereof, 5'-O-p-methoxytrityladenylyl(2',5')adenylyl(2',5')adenosine, xyloadenylyl(2',5')xyloadenylyl(2',5')xyloadenosine, (Rp)-P-thioadenylyl-(2',5')-(Sp)-thioadenylyl(2',5')adenosine, and (Sp)-P-thioadenylyl-(2',5')-(Rp)-thioadenylyl(2',5') adenosine.

Compounds of the present invention may be prepared using chemical enzymatic synthesis methods which will be apparent to one skilled in the art. For example, 2',5'-oligoadenylate-2'3'-cyclophosphates may be produced beginning with poly(A) with irregular 2',5' and 3',5' internucleotide bonds, using the procedure of Michaelson (A. M. Michaelson, The Chemistry of the Nucleosides and Nucleotides, 418–19 (1963)), by the chemical polymerization of 2' (3') adenosine monophosphate. The subsequent split of the 3'51 bonds in this polymer by ribonuclease leads to a monomer and 2,'5 oligoadenylates of varying lengths with a mixture containing a terminal 2',3' cyclophosphate group. By keeping the mixture at a low pH, the terminal cyclophosphate can be opened to provide other compounds useful in the method of this invention. Additional synthetic pathways useful in providing compound useful in the invention are disclosed in U.S. Pat. No. 4,981,957 to Lebleu et al., U.S. Pat. No. 4,708,935 to Suhadolnik et al., U.S. Pat. No. 4,990,498 to Suhadolnik et al., U.S. Pat. No. 4,515,781 to Torrence et al., and U.S. Pat. No. 4,476,301 to Imbach et al.

The active compounds described herein can, as noted above, be prepared in the form of their pharmaceutically acceptable salts. Pharmaceutically acceptable salts are salts that retain the desired biological activity of the parent compound and do not impart undesired toxicological effects. Examples of such salts include salts derived from bases, such as ammonium salts; alkali metal salts such as those of sodium and potassium; alkaline earth metal salts such as those of calcium and magnesium; and salts with organic bases such as triethylamine, dicyclohexylamine, and the like.

In order to enhance the intracellular transport of the active compounds, the compounds can also be conjugated to macromolecular carriers (e.g., poly(L-lysine)), as described in U.S. Pat. No. 5,405,939 to Suhadolnik et al.

The therapeutically effective dosage of any specific compound, the use of which is in the scope of present invention, will vary somewhat from compound to compound, patient to patient, and will depend upon the condition of the patient and the route of delivery. As a general proposition, a dosage from about 100 ng/kg to about 1 mg/kg will have therapeutic efficacy, with a dosage of from about 10 $\mu$g/kg to 100 $\mu$g/kg being preferred, with all weights being calculated based upon the weight of the active base, including the cases where a salt is employed. A dosage from about 10 $\mu$g/kg to about 10 mg/kg may be employed for oral administration, with a dosage from about 1 mg/kg to 10 mg/kg being preferred. Treatment can be administered once daily or several times per day for a period of 1 to 10 days or until the rhinoviral infection is essentially controlled. Lower doses given less frequently can be used to prevent or reduce the incidence of recurrence of the infection.

Depending on the solubility of the particular formulation of active compound administered, the daily dose may be divided among one or several unit dose administrations. The dose may be a single unit dose, which may, for example, be administered several times a week or from 1 to 3 times a day. Treatments may continue week to week on a chronic basis as necessary (i.e., the active agent can be administered repeatedly). Administration of the active compounds may be carried out therapeutically or prophylactically, but preferably the compounds are administered therapeutically, either before symptoms of the rhinoviral infection have appeared, or at a time when such symptoms are first appearing.

In accordance with the present method, an active compound as described herein may be prepared as a formulation suitable for oral, parenteral (including subcutaneous, intradermal, intramuscular, intravenous, and intraarticular), inhalation, rectal, topical (including buccal, sublingual, dermal and intraocular), and transdermal administration.

In the manufacture of a medicament according to the invention (a "formulation"), active agents or the pharmaceutically acceptable salts thereof (the "active compound") are typically admixed with, inter alia, an acceptable carrier. The carrier must, of course, be acceptable in the sense of being compatible with any other ingredients in the formulation and must not be deleterious to the subject. The carrier may be solid or liquid, or both, and is preferably formulated with the compound as a unit-dose formulation, for example, a tablet, which may contain from 0.05% to 99% by weight of the active compound. One or more active compounds may be incorporated in the formulations of the invention (e.g. the formulation may contain one or more additional antiviral agents as noted above), which formulations may be prepared by any of the well-known techniques if pharmacy consisting essentially of admixing the components, including one or more accessory therapeutic ingredients.

In addition to the active compounds or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 1 mg/mL. compositions that are soluble in water in an amount from about 1 mg/mL to about 60 mg/mL are defined as "partially soluble." For certain applications, water soluble compounds or salts may be desirable, whereas for other applications water-insoluble compounds or salts likewise may be desirable.

Pharmaceutical compositions may be prepared from the water-insoluble active compounds, or salts thereof, such as aqueous base emulsions. In such an instance, the composition will contain a sufficient amount of pharmaceutically acceptable emulsifying agent to emulsify the desired amount of the active compound or salt thereof. Particularly useful emulsifying agents include phosphatidyl cholines, and lecithin.

Further, the present invention provides liposomal formulations of the active compounds and salts thereof. The technology for forming liposomal suspensions is well known in the art. When the active compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the active compounds or salts thereof, may be lyophilized to produce a lyophilizate which may be reconstituted with a pharmaceutically acceptable carrier, such as water, to regenerate a liposomal suspension.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Preferably, formulations for oral administration may include enteric coatings known in the art to prevent degradation of the formulation in the stomach and provide release of the drug in the small intestine. Also, the dosage of the formulation may be raised slightly to overcome any digestion of the active compound in the gastrointestinal (GI) tract. Alternatively, a "diverting compound" (e.g., a 3',5'-oligoadenylate compound) may be administered in conjunction with the active compound in order to provide competing substrates for such GI enzymes.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection preparations of the active compound, which preparations are preferably isotonic with the blood of the intended recipient. These preparations may include antioxidants, buffers, bacteriostats, and solutes that render the formulation isotonic with the blood of the intended recipient. Aqueous and non-aqueous sterile suspensions may include suspending agents and thickening agents. The formulations may be presented in unit/dose or multi-dose containers, for example sealed ampules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Pharmaceutical formulations are also provided which are suitable for administration as an aerosol, by inhalation. These formulations comprise a solution or suspension of the desired active compound or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid active compound, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble active compound of the present invention or a salt thereof, in a carrier which comprises water. A surfactant may be present which lowers the surface tension of the formulation sufficiently to result in the formation of droplets within the desired size range when subjected to nebulization.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, e.g., *Pharmaceutical Research* 3, 318 (1986)) and typically take the form of an optionally buffered aqueous solution of the active compound.

The following examples are provided to illustrate the present invention, and should not be construed as limiting thereon. In these examples, M means molar, mM means millimolar, $\mu$M means micromolar, nm means nanomolar, ml means milliliters, $\mu$l means microliters, ° C. means degrees Celsius, g means grams, and $\mu$g means micrograms.

EXAMPLE 1

Experimental Materials

Cells: A-549 (human lung carcinoma) cells were obtained from the American Type Culture Collection (ATCC, Rockville, Md.). They were grown in Dulbecco's Minimum Essential Medium (DMEM, Gibco, Gaithersburg, Md.) supplemented with 10% fetal bovine serum (FBS, HyClone Laboratories, Logan, Utah). When the cells were infected with virus, the test medium contained 2% FBS with 0.1% $NaHCO_3$ and 50 $\mu$g gentamicin/ml.

Virus: Rhinovirus (RV) type 2, strain GPH was obtained from the ATCC. The virus was passed in cells and a pool prepared, ampuled, and frozen at −80° C. An aliquot of the frozen virus was titrated in A-549 cells prior to use in the following experiments.

Papirine: Papirine AIII was received in seven Eppendorf tubes from Dr. Edward I. Budowsky of the Department of Chemistry, Duke University (Durham, N.C.). The tubes were labeled PS-1A through PS-1G. An approximately $10^{-3}$M solution of the Papirine AIII was prepared by dissolving the contents of one tube in 3.75 ml of sterile saline. From this solution, 20 $\mu$l were diluted 1:100 in sterile water for injection. The optical density ascertained at a wave length of 260 nM ($OD_{260}$) for this solution was measured at 0.462. Using a standard ratio:proportion formula, with an $OD_{260}$ measurement of 0.370 equivalent to $10^{-5}$ M (10 $\mu$M), it was calculated that the original 1:100 Papirine A solution had a concentration of 12.49 $\mu$M.

A portion of the original solution was then diluted 1:3.95 in DMEM to provide a final concentration of 632 $\mu$M. One-half $\log_{10}$ dilutions of this solution yielded concentrations of 200, 63.2, 20, 6.3, 2.0, 0.63 $\mu$M when added to individual wells in microplates (see Example 2, below). When an equal volume of additional test medium used alone or containing virus was added to each well, this provided a final concentration of 316, 100, 31.6, 10, 3.16, 1.0 and 0.316 $\mu$M of Papirine A III.

Ribavirin, a known antiviral compound used in the following experiments as a positive control, was obtained from ICN Pharmaceuticals, Inc. (Costa Mesa, Calif.). This material was also initially dissolved in saline for use in the following experiments. Subsequent dilutions of ribavarin were made in the DMEM test medium described above.

EXAMPLE 2

Cytopathogenic Effect (CPE) Inhibition Assay

Papirine AIII was evaluated against a type 2 rhinovirus infection in A549 cells using two treatment methods. In both treatment methods, cells were plated in 96-well flatbottomed tissue culture microplates (Corning Glass Works, Corning, N.Y.) at $5\times10^4$ cells/well in DMEM growth medium, and incubated overnight at 37° C. to establish cell monolayers in each well. After incubation the medium was removed and varying concentrations of each drug (e.g. ribavarin, Papirine AIII) diluted in test medium were added to the appropriate wells (0.1 ml/well). Approximately 5–10 minutes later, four wells at each drug concentration were exposed to 0.1 ml of test medium with virus, with two additional wells exposed to 0.1 ml of sterile medium only, the latter to serve as toxicity controls. A group of 6 infected wells received no test compound to serve as virus controls, and 6 additional wells received sterile medium only as normal cell controls.

In the first treatment method, the test compound was added to the cells immediately prior to virus exposure and remained on the cells until viral cytopathogenic effect (CPE) was determined. In the second treatment method, fresh test compound (diluted in medium) was added to the cells daily, after removing the previous medium, until such time as the CPE was measured.

In order to compare two different samples of Papirine AIII, two experiments were conducted, with both methods being used in each experiment. In the first experiment, Papirine AIII taken from the tube labeled "PS-IA" was used as the test compound. Viral cytopathogenic effect (CPE) was determined following incubation at 37° C. in a humidified incubator with 5% $CO_2$ and 95% air atmosphere, when the CPE had reached maximal levels in the virus control wells as determined by microscopic examination (Day 5). In the second experiment, the test compound was taken from the tube labeled "PS-1B." In this second experiment, the CPE was fully developed by Day 3. Ribavarin was used as a positive control in both experiments.

The CPE from each well was scored from 0 (normal cells) to 4 (maximal, 100%, CPE). Morphological changes due to cytotoxicity were determined microscopically; this was graded as T (100% toxicity characterized by complete cell sloughing from plate), $P_{VH}$ (80% cytotoxicity), $P_H$ (60% cytotoxicity), P (40% cytotoxicity), $P_{SI}$ (20% cytotoxicity) and 0 (normal cells). Fifty percent effective (virus-inhibitory) doses ($ED_{50}$) and 50% cytotoxic doses ($CD_{50}$) were calculated by regression analysis for the CPE inhibition experiment. The therapeutic index (TI) was determined also by regression analysis of a line of best fit, this line calculated with drug concentration (in $\log_{10}$) on the x-axis and $\log_{10}$ reductions in virus on the y-axis.

The CPE inhibition data for both experiments are seen in Table 1.

TABLE 1

Effects of Papirine AIII on Rhinovirus Type 2 - Induced CPE Development in A549 Cells

| Compound | Drug Present without Medium Change | | | Drug Changed Every 24 hours | | |
|---|---|---|---|---|---|---|
| | $ED_{50}$ ($\mu$M) | $CD_{50}$ ($\mu$M) | TI[a] | $ED_{50}$ ($\mu$M) | $CD_{50}$ ($\mu$M) | TI[a] |
| Expt. 1[b] | | | | | | |
| PS-1A | 25 | >320 | >12 | 24 | >320 | >13 |
| Ribavirin | 610 | 2290 | 4 | 1190 | 2290 | 2 |
| Expt. 2[c] | | | | | | |
| PS-1B | 63 | >160 | >3 | 63 | >160 | >3 |
| Ribavirin | 410 | 740 | 2 | 186 | 740 | 4 |

[a]CD50/ED50
[b]Determined following 5 days' incubation at 37° C.
[c]Determined following 3 days' incubation at 37° C.

Both lots of Papirine AIII, PS-1A and PS-1B, were approximately equally inhibitory to the viral CPE, with the slightly decreased effect seen in Experiment 2 being within acceptable experimental error. Using both methods, significant inhibition of viral CPE was seen that exceeded the activity of the known positive inhibitor, ribavirin. Essentially the same efficacy was observed in both methods and in both experiments. Additionally, no cytotoxicity was observed in either experiment.

EXAMPLE 3

Effect of Papirine AIII on Rhinovirus Yield

After the second experiment, the microplate was frozen at −70° C., then thawed and the medium removed from the virus-infected wells and individually assayed for virus titer by adding 0.2 ml of serial 10-fold dilutions to a fresh monolayer of cells. The viral CPE, read 6 days later, was used as an infectivity endpoint. Table 2 summarizes the virus yield data.

TABLE 2

Effects of Papirine AIII on Rhinovirus Type 2 Virus Yield

| Compound | Drug Present without Medium Change | | | Drug Changed Every 24 hours | | |
|---|---|---|---|---|---|---|
| | $ED_{50}$ ($\mu$M) | $CD_{50}$ ($\mu$M) | TI[a] | $ED_{50}$ ($\mu$M) | $CD_{50}$ ($\mu$M) | TI[a] |
| PS-1B | 8 | >160 | >20 | 8 | >160 | >20 |
| Ribavirin[b] | 53 | 740 | 14 | 102 | 740 | 7 |

[a]$CD_{50}/ED_{50}$
[b]Ribavirin doses were converted from $\mu$g/ml to $\mu$M by the formula:
$$\frac{\text{Concentration} \times 1000}{244.2 \, (g/mol.) \times 1\, ml} = \mu M.$$

As the results indicate, Papirine AIII was more effective in reducing virus yield than it was in inhibiting viral CPE, since the $ED_{90}$ concentration was 8 $\mu$M when the virus was taken from the cells. The $ED_{90}$ was the same whether the compound was left on the cells or freshly added daily. The dose found to be effective in reducing virus yield by 1 $\log_{10}$ was determined to be 8 $\mu$M and 17 $\mu$M, depending on the method used. This activity resulted in a significant therapeutic index for this compound.

The use of fresh drug daily did not affect the antiviral activity of either Papirine AIII or ribavirin; ribavirin's activity was somewhat decreased by the medium change, and there was a slightly lesser activity.

Based upon these results, it was concluded that Papirine AIII is a significant inhibitor of type 2 rhinovirus.

The foregoing examples are illustrative of the present invention and are not to be construed as limiting thereof. The invention is defined by the following claims, with equivalents of the claims to be included therein.

That which is claimed is:

1. A method of combatting a rhinoviral infection in a subject in need of such treatment, comprising administering to said subject a compound of
Formula I:

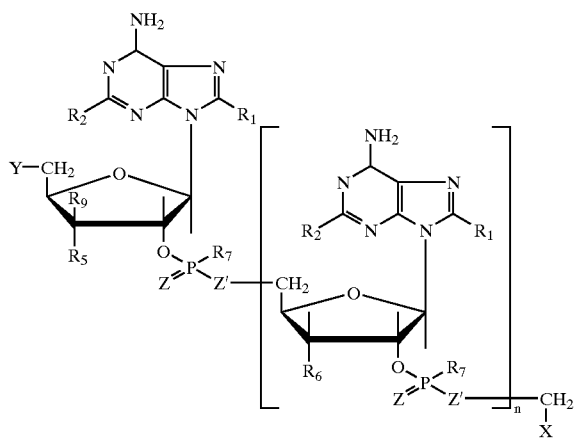

(I)

wherein n is 0, 1, 2, or 3;
each $R_1$ and $R_2$ is independently selected from the group consisting of hydrogen, halogen, and $N_3$;
each $R_5$ is independently hydrogen or —OH;
each $R_6$ is independently hydrogen or —OH;
$R_7$ is $O^-$ or —OH;
$R_9$ is hydrogen or —OH, with the proviso that when $R_9$ is —OH, $R_5$ is hydrogen;
Y is

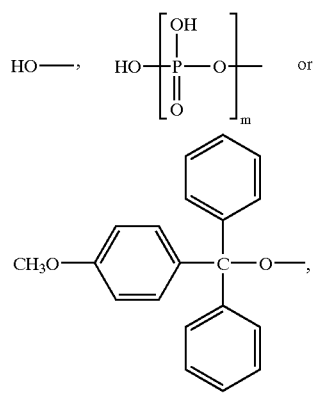

wherein m is 1, 2, or 3;
X is —CHOHCH$_2$OH, or is selected from the group consisting of

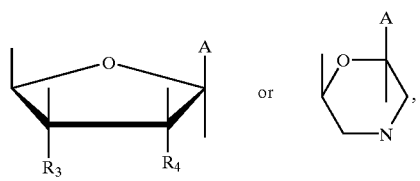

wherein $R_3$ and $R_4$ are each independently selected from the group consisting of hydrogen, —OH, and —PO$_4^{-2}$, or $R_3$ and $R_4$ together represent a cyclophosphate; and A is selected from the group consisting of:

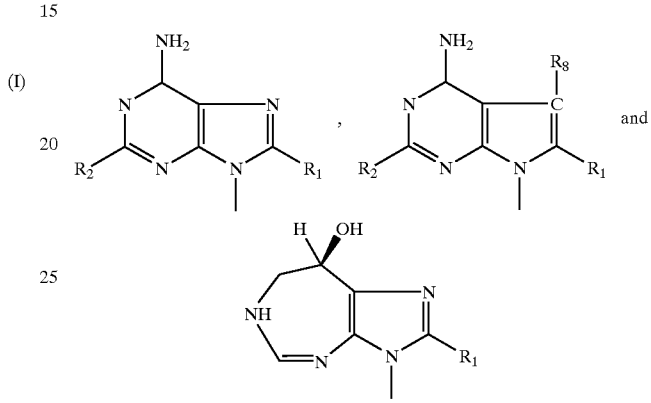

wherein each $R_1$ and $R_2$ are as provided above; and $R_8$ is selected from the group consisting of hydrogen, cyanogen, and amido;
each Z is independently O or S;
and each Z' is independently O or S;
or a pharmaceutically acceptable salt thereof;
said compound being administered in an amount effective to combat the rhinoviral infection.

2. The method according to claim 1, wherein Y is —OH; X is

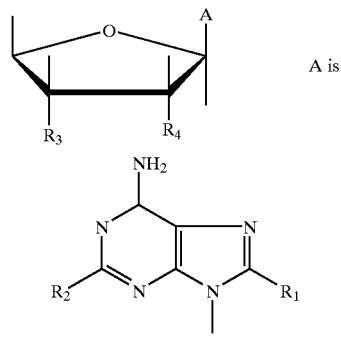

A is $R_1$ and $R_2$ are hydrogen;
$R_3$ is —OH and $R_4$ is —PO$_4^{-2}$, or
$R_3$ is PO$_4^{-2}$ and $R_4$ is —OH, or
$R_3$ and $R_4$ are both —OH, or
$R_3$ and $R_4$ together represent a cyclophosphate;
$R_5$ is —OH;
$R_9$ is hydrogen; and
Z and Z' are both O.

3. The method according to claim 1, wherein said subject is afflicted with a rhinoviral infection.

4. The method according to claim 1, wherein said subject is at risk of developing a rhinoviral infection and said compound is administered in a prophylactically effective amount.

5. A method according to claim 1, wherein said compound of Formula I is administered parenterally.

6. A method according to claim 1, wherein said compound of Formula I is administered orally.

7. A method according to claim 1, wherein said rhinoviral infection is caused by a rhinovirus selected from the group consisting of rhinovirus type 1 (RV-1), rhinovirus type 2 (RV-2), rhinovirus type 14 (RV-14), and rhinovirus type 39 (RV-39).

8. A method of combatting a rhinoviral infection in a subject in need of such treatment, comprising administering to said subject a compound of

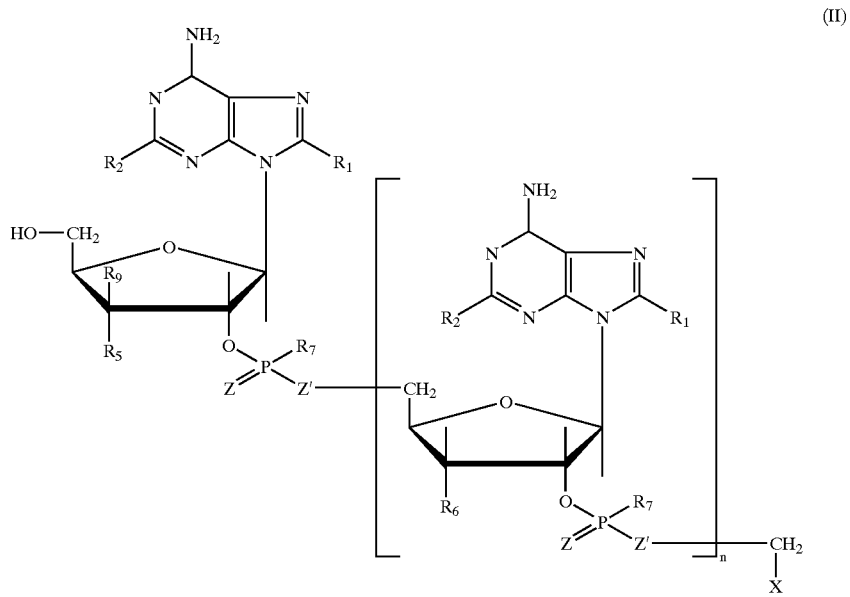

wherein n is 0, 1, 2, or 3;
each $R_1$ and $R_2$ is independently selected from the group consisting of hydrogen, halogen, and $N_3$;
$R_5$ is hydrogen or —OH;
$R_6$ is hydrogen or —OH;
$R_7$ is $O^-$ or —OH;
$R_9$ is hydrogen or —OH, with the proviso that when $R_9$ is —OH, $R_5$ is hydrogen;
X is —CHOHCH$_2$OH, or is selected from the group consisting of

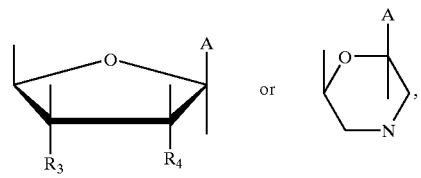

wherein $R_3$ and $R_4$ are each independently selected from the group consisting of hydrogen, —OH, and —PO$_4^{-2}$, or $R_3$ and $R_4$ together represent a cyclophosphate; and A is selected from the group consisting of:

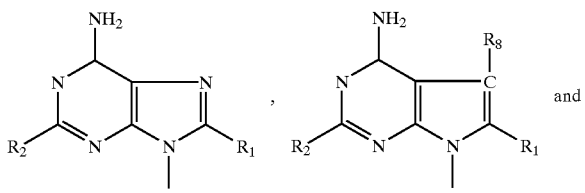

(II)

-continued wherein each $R^1$ and $R_2$ are as provided above; and
$R_8$ is selected from the group consisting of hydrogen, cyanogen, and amido;
each Z is independently O or S;
and each Z' is independently O or S;
or a pharmaceutically acceptable salt thereof;
said compound being administered in an amount effective to combat the rhinoviral infection.

9. The method according to claim 8, wherein said subject is afflicted with a rhinoviral infection.

10. The method according to claim 8, wherein said subject is at risk of developing a rhinoviral infection and said compound is administered in a prophylactically effective amount.

11. A method according to claim 8, wherein said compound of Formula II is administered parenterally.

12. A method according to claim 8, wherein said compound of Formula II is administered orally.

13. A method according to claim 8, wherein said rhinoviral infection is caused by a rhinovirus selected from the group consisting of rhinovirus type 1 (RV-1), rhinovirus type 2 (RV-2), rhinovirus type 14 (RV-14), and rhinovirus type 39 (RV-39).

14. A method of combatting a rhinoviral infection in a subject in need of such treatment, comprising administering to said subject a compound of

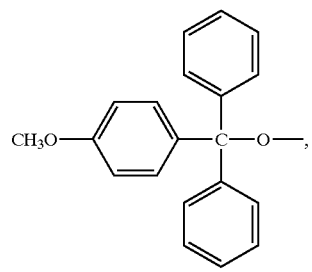

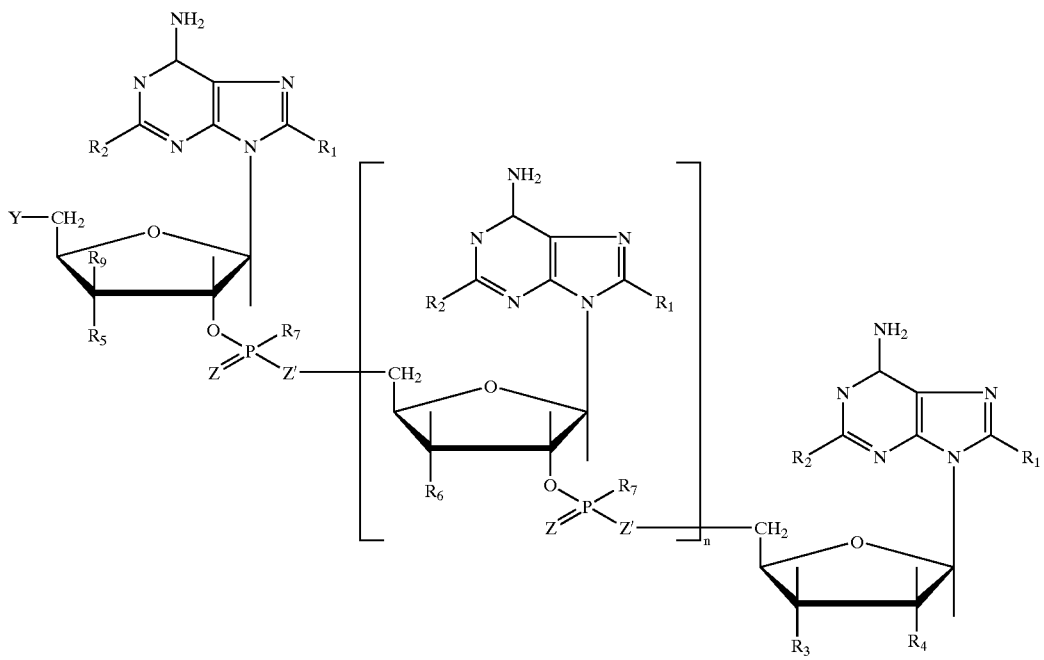

wherein n is 0, 1, 2, or 3;

each $R_1$ and $R_2$ is independently selected from the group consisting of hydrogen, halogen, and $N_3$;

$R_3$ and $R_4$ are each independently selected from the group consisting of hydrogen, —OH, and —$PO_4^{-2}$, or $R_3$ and $R_4$ together represent a cyclophosphate;

$R_5$ is hydrogen or —OH;

$R_6$ is hydrogen or —OH;

$R_7$ is $O^-$ or —OH;

$R_9$ is hydrogen or —OH, with the proviso that when $R_9$ is —OH, $R_5$ is hydrogen;

Y is

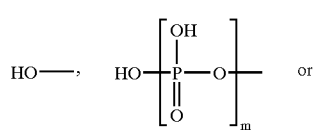

wherein m is 1, 2, or 3;

each Z is independently O or S;

and each Z' is independently O or S;

or a pharmaceutically acceptable salt thereof; said compound being administered in an amount effective to combat the rhinoviral infection.

15. The method according to claim 14, wherein said subject is afflicted with a rhinoviral infection.

16. The method according to claim 14, wherein said subject is at risk of developing a rhinoviral infection and said compound is administered in a prophylactically effective amount.

17. A method according to claim 14, wherein said compound of Formula III is administered parenterally.

18. A method according to claim 14, wherein said compound of Formula III is administered orally.

19. A method according to claim 14, wherein said rhinoviral infection is caused by a rhinovirus selected from the group consisting of rhinovirus type 1 (RV-1), rhinovirus type 2 (RV-2), rhinovirus type 14 (RV-14), and rhinovirus type 39 (RV-39).

20. A pharmaceutical formulation for the combatting of rhinoviral infections comprising a compound of Formula I:

(I)

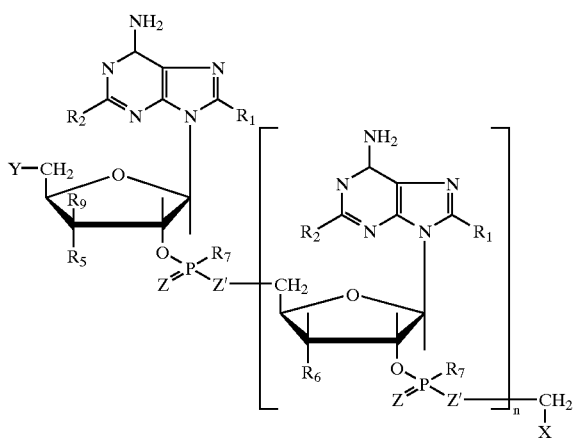

wherein n is 0, 1, 2, or 3;
each $R_1$ and $R_2$ is independently selected from the group consisting of hydrogen, halogen, and $N_3$;
each $R_5$ is independently hydrogen or —OH;
each $R_6$ is independently hydrogen or —OH;
$R_7$ is $O^-$ or —OH;
$R_9$ is hydrogen or —OH, with the proviso that when $R_9$ is —OH, $R_5$ is hydrogen;
Y is

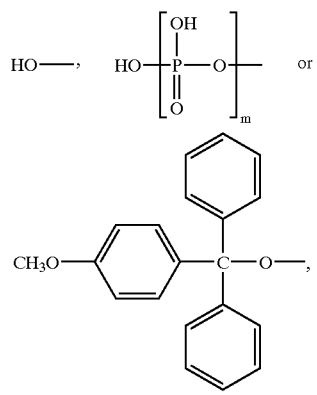

wherein m is 1, 2, or 3;
X is —CHOHCH$_2$OH, or is selected from the group consisting of

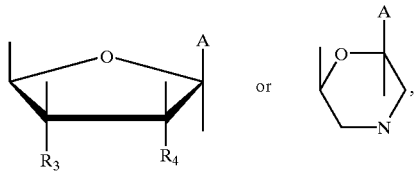

wherein $R_3$ and $R_4$ are each independently selected from the group consisting of hydrogen, —OH, and —PO$_4^{-2}$, or $R_3$ and $R_4$ together represent a cyclophosphate; and A is selected from the group consisting of

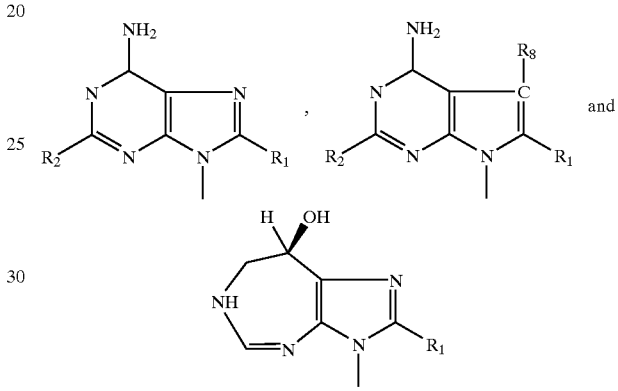

wherein each $R_1$ and $R_2$ are as provided above; and $R_8$ is selected from the group consisting of hydrogen, cyanogen, and amido;

each Z is independently O or S;
and each Z' is independently O or S;

or a pharmaceutically acceptable salt thereof, in a pharmaceutically acceptable carrier.

* * * * *